United States Patent [19]
Gehring et al.

[11] Patent Number: 4,770,688
[45] Date of Patent: Sep. 13, 1988

[54] 5-AZIDO- OR 5-PHOSPHOROIMIDO-1-ARYL-PYRAZOLES, COMPOSITION CONTAINING THEM, AND HERBICIDAL AND PLANT GROWTH REGULATING METHODS OF USING THEM

[75] Inventors: Reinhold Gehring, Wuppertal; Markus Lindig, Hilden; Otto Schallner, Monheim; Jörg Stetter, Wuppertal; Hans-Joachim Santel, Leverkusen; Robert R. Schmidt; Klaus Lürssen, both of Bergisch, all of Fed. Rep. of Germany

[73] Assignee: Bayer Aktiengesellschaft, Leverkusen, Fed. Rep. of Germany

[21] Appl. No.: 942,141

[22] Filed: Dec. 16, 1986

[30] Foreign Application Priority Data

Dec. 20, 1985 [DE] Fed. Rep. of Germany ....... 3545347

[51] Int. Cl.$^4$ .................. A01N 31/675; A01N 43/56; C07D 403/04; C07F 9/65

[52] U.S. Cl. .......................................... 71/86; 71/87; 71/92; 546/22; 546/24; 546/279; 548/115; 548/374

[58] Field of Search .................... 548/115, 374; 71/92, 71/86, 87; 546/22, 24, 279

[56] References Cited

FOREIGN PATENT DOCUMENTS

| | | | |
|---|---|---|---|
| 3226513 | 2/1983 | Fed. Rep. of Germany .......... | 71/92 |
| 1337497 | 11/1973 | United Kingdom .................... | 71/92 |
| 2123420 | 2/1984 | United Kingdom .................... | 71/92 |
| 2136427 | 9/1984 | United Kingdom .................... | 71/92 |

OTHER PUBLICATIONS

Chemical Abstracts, vol. 99, No. 9, Aug. 29, 1983, p. 618, Abstract 99:70618a Pyrazole Derivatives. . . .

Chemische Berichte, vol. 117, No. 2, Feb. 3, 1984, pp. 585–621—See p. 587, Compound 10c.

"Fused Pyrazolopyrimidines. I.", J. Heterocyclic Chem., 17, (1980), pp. 1603–1604.

"Pyrazole Derivatives I. Synthesis of Some Cyanopyrazoles", Rev. Latinoam. Quim. 13, (1982), pp. 100–102.

*Primary Examiner*—Richard A. Schwartz
*Assistant Examiner*—Kurt G. Briscoe
*Attorney, Agent, or Firm*—Sprung Horn Kramer & Woods

[57] ABSTRACT

A 1-aryl-pyrazole of the formula

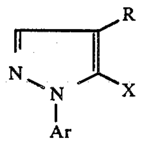

in which

R represents cyano or nitro,

Ar represents in each case optionally substituted phenyl or pyridyl,

X represents an azido group, or represents the radical

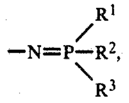

and $R^1$, $R^2$ and $R^3$ each independently represents alkyl, alkenyl, alkinyl, halogenoalkyl, alkoxy, alkoxyalkyl, cycloalkyl or cycloalkyloxy, or represents in each case optionally substituted aryl, aryloxy, aralkyl or aralkyloxy, but wherein, in the case where R represents cyano and X simultaneously represents an azido group, Ar does not represent unsubstituted phenyl and does not represent 5-nitro-2-pyridyl. The compounds exhibit herbicidal and plant growth-regulating activity.

10 Claims, No Drawings

5-AZIDO- OR 5-PHOSPHOROIMIDO-1-ARYLPYRAZOLES, COMPOSITION CONTAINING THEM, AND HERBICIDAL AND PLANT GROWTH REGULATING METHODS OF USING THEM

The invention relates to 1-aryl-pyrazoles, several processes for their preparation and their use as herbicides and plant growth regulators.

It is known that certain 1-aryl-pyrazoles, such as, for example, 4-cyano-5-propionamideo-1-(2,4,6-trichlorophenyl)-pyrazole, have herbicidal properties (compare DE-OS (German Published Specification) No. 3,226,513).

The herbicidal activity of these already known compounds against weeds, however, like their tolerance towards important crop plants, is not always completely satisfactory in all fields of use.

It is furthermore known that the compounds 5-azido-4-cyano-1-phenyl-pyrazole and 5-azido-4-cyano-1-(5-nitro-2-pyridyl)-pyrazole are described as intermediate products (compare J. Heterocyl. Chem. 17, 1603–1604 [1980] and Rev. Latinoam. Quim. 13, 100–102 [1982]). However, nothing is known of a herbicidal or plant growth-regulating activity of these compounds which have already been described.

New 1-aryl-pyrazoles of the general formula (1),

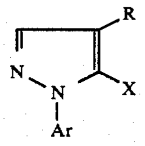

(I)

in which

R represents cyano or nitro,

Ar represents in each case optionally substituted phenyl or pyridyl and

X represents an azido group, or represents a radical

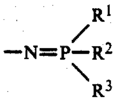

wherein $R^1$, $R^2$ and $R^3$ independently of one another each represent alkyl, alkenyl, alkinyl, halogenalkyl, alkoxy, alkoxyalkyl, cycloalkyl or cycloalkyloxy, or represent in each case optionally substituted aryl, aryloxy, aralkyl or aralkyloxy, but wherein, in the case where R represents cyano and X simultaneously represents an azido group, Ar does not represent unsubstituted phenyl and does not represent 5-nitro-2-pyridyl, have been found.

It has furthermore been found that the new 1-aryl-pyrazoles of the general formula (I)

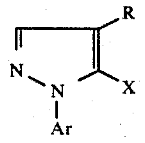

(I)

in which

R represents cyano or nitro,

Ar represents in each case optionally substituted phenyl or pyridyl and

X represents an azido group, or represents a radical

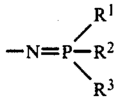

wherein $R^1$, $R^2$ and $R^3$ independently of one another each represent alkyl, alkenyl, alkinyl, halogenalkyl, alkoxyalkyl, cycloalkyl, alkoxy, cycloalkyloxy or represent in each case optionally substituted aryl, aryloxy, aralkyl or aralkyloxy, but wherein, in the case where R represents cyano and X simultaneously represents an azido group, Ar does not represent unsubstituted phenyl and does not represent 5-nitro-2-pyridyl, are obtained by a process in which (a-α) 5-halogen-1-aryl-pyrazoles of the formula (II)

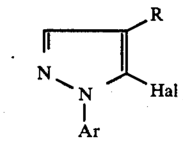

(II)

in which

R and Ar have the abovementioned meaning and

Hal represents halogen, are reacted with alkali metal azides of the formula (III)

$M^{\oplus}\text{-}N_3^{\ominus}$ (III)

in which $M^{\oplus}$ represents an alkali metal cation, if appropriate in the presence of a diluent, or by a process in which (a-β) 5-hydrazino-1-aryl-pyrazoles of the formula (IV)

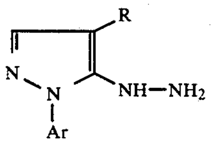

(IV)

in which

R and Ar have the abovementioned meaning, are diazotized with alkali metal nitrites of the formula (V)

$M^{\oplus}\text{-}NO_2^{\ominus}$ (V)

in which $M^{\oplus}$ represents an alkali metal cation, in the presence of a catalyst acid and if appropriate in the presence of a diluent, or by a process in which (b) the 5-azido-1-arylpyrazoles obtainable by process (a-α) or (a-β), of the formula (Ia)

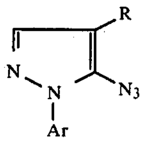

(Ia)

in which

R and Ar have the abovementioned meaning, are reacted in a second stage with phosphines or phosphites of the formula (VI)

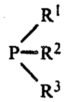

(VI)

in which $R^1$, $R^2$ and $R^3$ have the abovementioned meaning, if appropriate in the presence of a diluent.

Finally, it has been found that the new 1-aryl-pyrazoles of the general formual (I) have herbicidal, and in particular selective herbicidal, and plant growth-regulating properties.

Surprisingly, the 1-aryl-pyrazoles of the general formula (I) according to the invention exhibit, in addition to a considerably better general herbicidal activity against weeds, at the same time a considerably higher tolerance towards crop plants and moreover, additionally completely surprisingly, also plant growth-regulating properties, in comparison with the 1-aryl-pyrazoles known from the prior art, such as, for example, 4-cyano-5-propionamido-1-(2,4,6-trichlorophenyl)-pyrazole, which are closely related compounds chemically and from the point of view of their action.

Formula (I) provides a general definition of the 1-aryl-pyrazoles according to the invention. Preferred 1-aryl-pyrazoles of the formula (I) are those in which R represents cyano or nitro, Ar represents phenyl, 2-pyridyl, 3-pyridyl or 4-pyridyl, in each case optionally monosubstituted or poly-substituted by identical or different substituents, possible substituents in each case being: cyano, nitro, halogen, in each case straight-chain or branched alkyl, alkoxy or alkoxycarbonyl with in each case up to 4 carbon atoms, in each case straight-chain or branched halogenalkyl or halogenalkoxy with in each case 1 to 4 carbon atoms and 1 to 9 identical or different halogen atoms and the radical $-S(O)_n-R^4$, X represents an azido group or represents a radical

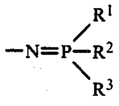

wherein $R^1$, $R^2$ and $R^3$ independently of one another represent in each case straight-chain or branched alkyl, alkenyl, or alkinyl with in each case up to 8 carbon atoms, or represent straight-chain or branched halogenalkyl with 1 to 6 carbon atoms and 1 to 13 identical or different halogen atoms, or represent straight-chain or branched alkoxyalkyl with in each case 1 to 4 carbon atoms in the individual alkyl parts, or represent straight-chain or branched alkoxy with 1 to 6 carbon atoms, or represent cycloalkyl or cycloalkoxy with in each case 3 to 7 carbon atoms, or represent aralkyl, aralkoxy, aryl or aryloxy with in each case 6 to 10 carbon atoms in the individual aryl parts and, where appropriate, 1 to 3 carbon atoms in the straight-chain or branched alkyl parts and in each case optionally monosubstituted or polysubstituted by identical or different substituents in the aryl parts, possible substituents on the aryl in each case being: halogen, cyano, nitro and in each case straight-chain or branched alkyl, alkoxy, alkylthio or halogenalkyl with in each case 1 to 4 carbon atoms, in the case of the halogenalkyl, with 1 to 9 identical or different halogen atoms, $R^4$ represents amino, or represents in each case straight-chain or branched alkyl, alkylamino, dialkylamino or halogenalkyl with in each case up to 4 carbon atoms in the individual alkyl parts and, in the case of the halogenalkyl, with up to 9 identical or different halogen atoms, and n represents the number 0, 1 or 2, but wherein, in the case where R represents cyano and X simultaneously represents an azido group, Ar does not represent unsubstituted phenyl and does not represent 5-nitro-2-pyridyl.

Particularly preferred compounds of the formula (I) are those in which

R represents cyano or nitro.

Ar represents phenyl which is optionally mono-, di-, tri-, tetra- or pentasubstituted by identical or different substituents, or represents 2-pyridyl which is optionally mono-, di-, tri- or tetrasubstituted by identical or different substituents, possible substituents in each case being: cyano, nitro, fluoro, chloro, bromo, iodo, methyl, ethyl, n- and i-propyl, n-, i-, s- and t-butyl, or represents methoxy, ethoxy, methoxycarbonyl, ethoxycarbonyl, trifluoromethyl, trichloromethyl,, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethyoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy and the radical $-S(O)_n-R^4$ and X represents an azido group, or represents a radical

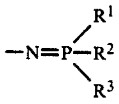

wherein $R^1$, $R^2$ and $R^3$ independently of one another each represent methyl, ethyl, n- or i-propyl, n-, i-, s- or t-butyl, allyl, propargyl, chloromethyl, dichloromethyl, trichloromethyl, fluoromethyl, dichlorofluoromethyl, trifluoromethyl, dichlorofluoromethyl, difluorochloromethyl, chloroethyl, trichloroethyl, pentachloroethyl, trifluoroethyl, pentafluoroethyl, bromoethyl, methoxymethyl, methoxyethyl, ethoxymethyl, ethoxyethyl, n- propoxymethyl, i-propoxymethyl, n-propoxyethyl, i-propoxyethyl, methoxy, ethoxy, n- or i-propoxy, n-, i-, s- or t-butoxy, cyclopropyl, cyclopentyl, cyclohexyl or cyclohexyloxy, or represents benzyl, benzyloxy, phenyl or phenoxy, in each case optionally mono-, di-, tri-, tetra- or pentasubstituted by identical or different substituents, possible substituents on the aryl in each case being: fluorine, chlorine, bromine, cyano, nitro, methyl, ethyl, methoxy, methylthio and trifluoromethyl, $R^4$ represents amino, methylamino, ethylamino, dimethylamino, diethylamino, fluorodichloromethyl, difluoromethyl, tetrafluoroethyl, trichloroethyl, trifluoromethyl, methyl or ethyl and n represents the number 0, 1 or 2, but wherein, in the case where R represents cyano and X simultaneously represents an azido group, Ar does not represent unsubstituted phenyl and does not represent 5-nitro-2-pyridyl.

Especially preferred compounds of the formula (I) are those in which

R represents cyano or nitro,

Ar represents phenyl which is optionally mono-. di-, tri-, tetra- or pentasubstituted by identical or different substituents or represents 2-pyridyl which is optionally mono-, di-, tri- or tetrasubstituted by identical or different substituents, possible substituents in each case being: cyano, nitro, fluoro, chloro, bromo, iodo, methyl, ethyl, n- and i-propyl, n-, i-, s- and t-butyl, or represents methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy and the radical $-S(O)_n-R^4$ and X represents an azido group, or represents a radical

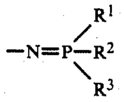

wherein $R^1$, $R^2$ and $R^3$ independently of one another each represent methyl, ethyl, n- or i-propyl, n-, i-, s- or t-butyl, methoxy, ethoxy, n- or i-propoxy or n-, i-, s- or t-butoxy, or represent benzyl, benzyloxy, phenyl or phenoxy, in each case optionally mono-, di-, tri-, tetra- or pentasubstituted by identical or different substituents, possible substituents on the aryl in each case being: fluorine, chlorine, bromine, cyano, nitro, methyl, ethyl, methoxy, methylthio and trifluoromethyl, $R^4$ represents amino, methylamino, ethylamino, dimethylamino, diethylamino, fluorodichloromethyl, difluoromethyl, tetrafluoroethyl, trichloroethyl, trifluoromethyl, methyl or ethyl and n represents the number 0, 1 or 2, but wherein, in the case where R represents cyano and X simultaneously represents an azido group, Ar does not represent unsubstituted phenyl and does not represent 5-nitro-2-pyridyl.

The following substituted 1-aryl-pyrazoles of the general formula (I) may be mentioned specifically, in addition to the compounds mentioned in the preparation examples:

TABLE 1

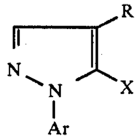 (I)

| R | X | Ar |
|---|---|---|
| CN | $N_3$ | 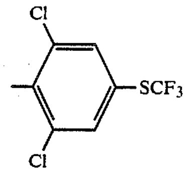 |
| $NO_2$ | $N_3$ | 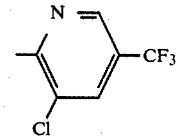 |
| $NO_2$ | $N_3$ | 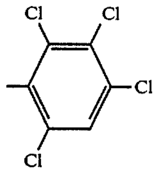 |
| CN | 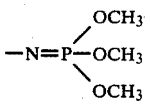 | 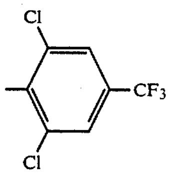 |
| $NO_2$ | 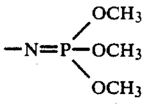 | 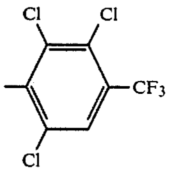 |
| $NO_2$ | 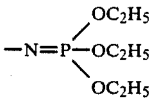 | 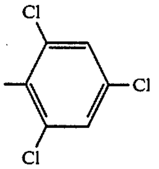 |
| $NO_2$ | 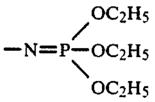 | 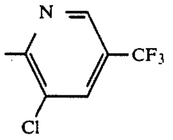 |

TABLE 1-continued

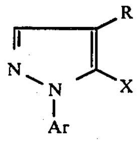
(I)

| R | X | Ar |
|---|---|---|
| CN | 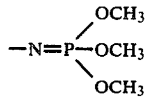 | 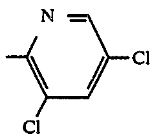 |
| $NO_2$ | $N_3$ | 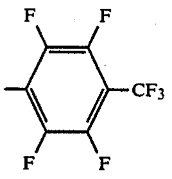 |
| $NO_2$ | 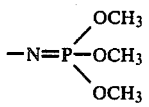 | 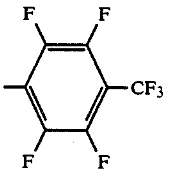 |
| $NO_2$ | 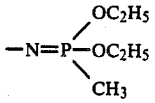 | 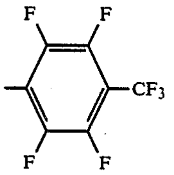 |
| CN | $-N=P(C_6H_5)_3$ | 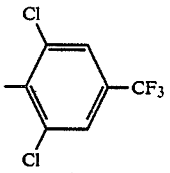 |
| $NO_2$ | $N_3$ | 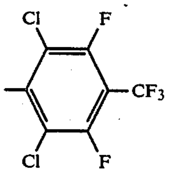 |
| $NO_2$ | $-N=P(OC_2H_5)_3$ | 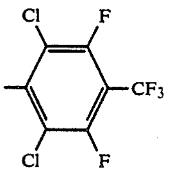 |
| $NO_2$ | 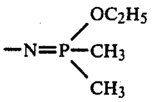 | 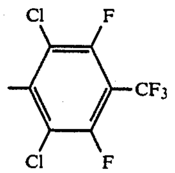 |

TABLE 1-continued

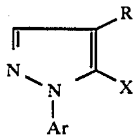
(I)

| R | X | Ar |
|---|---|---|
| $NO_2$ | $-N=P(C_6H_5)_3$ | 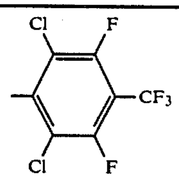 |
| CN | 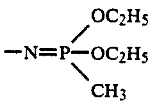 | 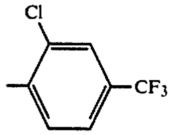 |
| CN | 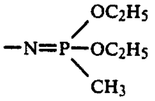 | 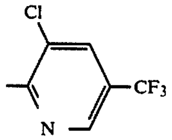 |

If, for example, 5-bromo-4-nitro-1-(2,3,6-trichloro-4-trifluoromethyl-phenyl)-pyrazole and sodium azide are used as starting compounds, the course of the reaction in process (a-α) according to the invention can be represented by the following equation:

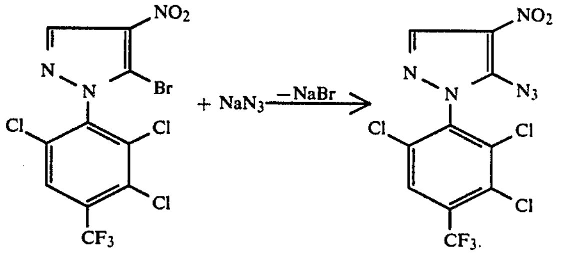

If, for example, 4-cyano-5-hydrazino-1-(2,4-dichlorophenyl)-pyrazole and sodium nitrite are used as starting substances and hydrochloric acid is used as the catalyst, the course of the reaction in process (a-β) according to the invention can be represented by the following equation:

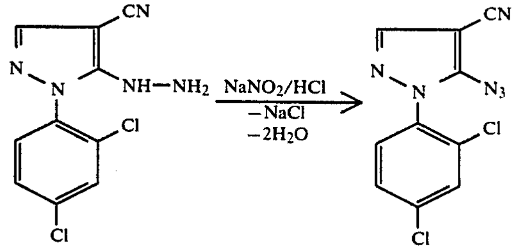

If, for example, 5-azido-4-cyano-1-(2,4-dichlorophenyl)-pyrazole and triethylphosphite are used as starting substances, the course of the reaction in process (b) according to the invention can be represented by the following equation:

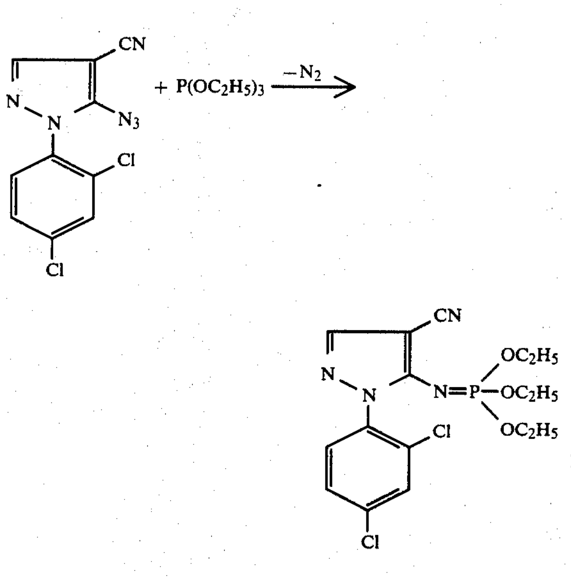

Formula (II) provides a general definition of the 5-halogeno-1-aryl-pyrazoles required as starting substances for carrying out process (a-α) according to the invention. In this formula (II), R and Ar preferably represent those radicals which have already been mentioned as preferred for these substituents in connection with the description of the substances of the formula (I) according to the invention. Hal preferably represents chlorine or bromine.

The 5-halogeno-1-aryl-pyrazoles of the formula (II) are in part the subject of commonly assigned application Ser. No. 816,643, filed Jan. 6, 1986, now pending, Ser. No. 866,050, filed May 22, 1986, now pending, and Ser. No. 866,638, filed May 22, 1986, now pending, corresponding respectively to DE-P No. 3,501,323 of Jan. 17, 1985, DE-P No. 3,520,329 of June 7, 1985 and DE-P No. 3,520,330 of June 7, 1985.

They are obtained, for example, by a process in which 5-amino-1-aryl-pyrazoles of the formula (VII)

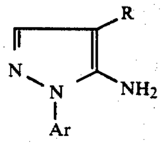
(VII)

in which

R and Ar have the abovementioned meaning, are diazotized with nitrite compounds of the formula (VIII)

$R^5—O—N=O$ (VIII)

in which $R^5$ represents hydrogen or alkyl, or represents an alkali metal cation, in the presence of a hydrogen halide acid, such as, for example, hydrochloric acid or hydrobromic acid, or in the presence of a haloform, such as, for example, chloroform or bromoform, at temperatures between −20° C. and +80° C., in the customary manner (compare, for example, "Organikum" 15th edition, VEB Deutscher Verlag der Wissenschaften, Berlin 1981 page 652, et seq; J. Chem. Soc. C, 1966, 1249 or Rev. Latinoam. Quim. 13, 100–102 [1982]).

The 5-amino-1-aryl-pyrazoles of the formula (VII) are known in some cases (compare, for example, European Pat. No. 26,034, European Pat. No. 53,678 or European Pat. No. 34,945, and DE-OS (German Published Specification) No. 3,402,308, DE-OS (German Published Specification) No. 3,226,496, DE-OS (German Published Specification) No. 3,408,727 or DE-OS (German Published Specification) No. 3,420,985), and some of them are the subject of commonly assigned patent applications Ser. No. 690,347, supra. and Ser. No. 866,638, filed May 22, 1986 now pending, corresponding to DE-P No. 3,520,327 of June 7, 1985, and the preparation examples hereinbelow.

They are obtained, for example, by a process in which aryl-hydrazines of the formula (IX)

$Ar—NH—NH_2$ (IX)

in which

Ar has the abovementioned meaning, (α) and acrylonitrile derivatives of the formula (X)

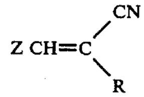
(X)

in which

R has the abovementioned meaning and

Z represents halogen, hydroxyl, alkoxy or dialkylamino, (β) 2-halogenoacrylonitriles of the formula (XI)

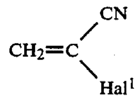
(XI)

in which $Hal^1$ represents halogen, in particular chlorine or bromine, are either initially reacted in a first stage, if appropriate in the presence of a diluent, such as, for example, glacial acetic acid or ethanol, and if appropriate in the presence of a reaction auxiliary, such as, for example, sodium acetate, at temperatures between −20° C. and +20° C., to give the arylhydrazine derivatives of the formula (XII)

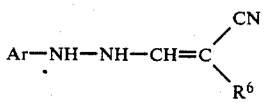
(XII)

in which

Ar and $R^1$ have the abovementioned meaning and $R^6$ represents halogen, cyano or nitro, and these are cyclized in a second stage, if appropriate in the presence of a diluent, such as, for example, ethyleneglycolmonoethyl ether, and if appropriate in the presence of an acid catalyst, such as, for example, sulphuric acid or phosphoric acid, at temperatures between +50° C. and +150° C., or are cyclized directly in one reaction step, without isolation of the intermediate stage of the formula (XII), if appropriate in the presence of a diluent, for example ethyleneglycolmonoethyl ether or ethanol, at temperatures between +50° C. and +150° C., and, if appropriate, the 5-aminopyrazoles which are obtainable by variant (β) and are unsubstituted in the 4-position, of the formula (XIII)

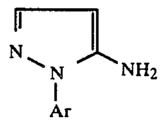

(XIII)

in which

Ar has the abovementioned meaning, are nitrated in a subsequent reaction with a nitrating agent, such as, for example, nitric acid, if appropriate in the presence of a diluent, such as, for example, glacial acetic acid, and if appropriate in the presence of a reaction auxiliary, such as, for example, acetic anhydride, at temperatures between −20° C. and +50° C.

If appropriate, it may be of advantage here for the amino group in the 5-position of the pyrazole ring to be protected with the aid of customary protective group techniques, for example by acylation, before the nitration reaction and, when the nitration has taken place, for the amino-protective group to be split off again, likewise in the customary manner, for example by hydrolysis with an aqueous or alcoholic base.

The arylhydrazines of the formula (IX) are known (compare, for example, U.S. Pat. No. 4,127,575; U.S. Pat. No. 3,609,158; DE-OS (German Published Specification) No. 2,558,399; and J. Chem. Soc. C, 1971, 167–174) or they can be obtained by known processes in a simple analogous manner (compare, for example, Houben-Weyl "Methoden der organischen Chemie" "Methods of Organic Chemistry") volume X/2, page 203, Thieme Verlag Stuttgart, 1967), by a process in which, for example, the known anilines or pyridylamines of the formula (XIV)

$$Ar—NH_2 \qquad (XIV)$$

in which

Ar has the abovementioned meaning, are reacted with sodium nitrite in the presence of of an acid, such as, for example, sulphuric acid, and then with tin-II-chloride likewise in the presence of an acid, such as, for example, hydrochloric acid, at temperatures between −20° C. and +80° C., or by a process in which halogenoaromatics of the formula (XV)

$$Ar—Hal^2 \qquad (XV)$$

in which

Ar has the abovementioned meaning and $Hal^2$ represents halogen, in particular fluorine, chlorine or bromine, are reacted with hydrazine hydrate, if appropriate in the presence of a diluent, such as, for example, pyridine or dioxane, at temperatures between 0° C. and 150° C.

The nitrite compounds of the formula (VIII), the acrylonitrile derivative of the formula (X), the 2-halogenoacrylonitriles of the formula (XI), the anilines and pyridylamines of the formula (XIV) and the halogenaromatics of the formula (XV) are generally known compounds of organic chemistry.

Formula (III) provides a general definition of the alkali metal azides furthermore required as starting substances for carrying out process (a-α) according to the invention. In this formula (III), $M^{\oplus}$ preferably represents a sodium or potassium cation.

The alkali metal azides of the formula (III) are generally known compounds.

Formula (IV) provides a general definition of the 5-hydrazino-1-aryl-pyrazoles required as starting substances for carrying out process (a-β) according to the invention. In this formula (IV), R and Ar preferably represent those radicals which have already been mentioned as preferred for these substituents in connection with the description of the substances of the formula (I) according to the invention.

The 5-hydrazino-1-aryl-pyrazoles of the formula (IV) are the subject of commonly assigned application Ser. No. 885,051, filed July 14, 1986, now pending, corresponding to DE-P No. 3,528,478 of Aug. 8, 1985.

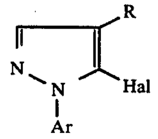

(II)

in which

R and Ar have the abovementioned meaning and

Hal represents halogen, in particular chlorine or bromine, are reacted with hydrazine hydrate, if appropriate in the presence of a diluent, such as, for example, dioxane, at temperatures between 50° C. and 120° C.

Formula (V) provides a general definition of the alkali metal nitrites furthermore required as starting substances for carrying out process (a-β) according to the invention. In this formula (V) $M^{\oplus}$ preferably represents a sodium or potassium cation.

The alkali metal nitrites of the formula (V) are generally known compounds.

Formula (Ia) provides a general definition of the 5-azido-1-aryl-pyrazoles required as starting substances for carrying out process (b) according to the invention. In this formula (Ia), R and Ar preferably represent those radicals which have already been mentioned as preferred for these substituents in connection with the description of the substances of the formula (I) according to the invention.

The 5-azido-1-aryl-pyrazoles of the formula (Ia) are compounds according to the invention and are obtainable with the aid of processes (a-α) or (a-β) according to the invention.

Formula (VI) supplies a general definition of the phosphines and phosphites furthermore required as starting substances for carrying out process (b) according to the invention. In this formula (VI), $R^1$, $R^2$ and $R^3$ preferably represent those radicals which have already been mentioned as preferred for these substituents in connection with the description of the substances of the formula (I) according to the invention.

The phosphines and phosphites of the formula (VI) are generally known compounds of organic chemistry.

Possible diluents for carrying out process (a-α) according to the invention are the inert organic solvents.

These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform or carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethyl phosphoric acid triamide, esters, such as ethyl acetate, or sulphoxides, such as dimethylsulphoxide.

Dimethylsulphoxide is particularly preferably used as the diluent.

The reaction temperatures can be varied within a substantial range in carrying out process (a-$\alpha$) according to the invention. The reaction is in general carried out at temperatures between $-20°$ C. and $+80°$ C., preferably at temperatures between 0° C. and $+50°$ C.

For carrying out process (a-$\alpha$) according to the invention, in general 1.0 to 5.0 mols, preferably 1.0 to 2.0 mols, of alkali metal azide of the formula (III) are employed per mole of 5-halogeno-1-aryl-pyrazole of the formula (II). The 5-azido-1-aryl-pyrazoles of the formula (Ia) are worked up, isolated and characterized by generally customary processes.

Possible diluents for carrying out process (a-$\beta$) according to the invention are chiefly water or aqueous acids, such as, for example, aqueous hydrochloric acid, which in this case is simultaneously used as the diluent and as the catalyst acid.

Process (a-$\beta$) according to the invention is carried out in the presence of an inorganic acid as a catalyst. Catalysts which are preferably used are strong mineral acids, and particularly preferably hydrochloric acid.

The reaction temperatures can be varied within a substantial range in carrying out process (a-$\beta$) according to the invention. The reaction is in general carried out at temperatures between $-30°$ C. and $+50°$ C., preferably at temperatures between $-20°$ C. and $+30°$ C.

For carrying out process (a-$\beta$) according to the invention, 1.0 to 2.5 mols, preferably 1.0 to 1.5 mols, of alkali metal nitrite of the formula (V) are employed per mol of 5-hydrazino-1-aryl-pyrazole of the formula (IV). The reaction is carried out and the 5-azido-1-aryl-pyrazoles of the formula (Ia) are worked up and isolated by generally customary processes.

Possible diluents for carrying out process (b) according to the invention are the inert organic solvents.

These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform or carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethyl phosphoric acid triamide, esters, such as ethyl acetate, or sulphoxides, such as dimethylsulphoxide.

The reaction temperatures can be varied within a substantial range in carrying out process (b) according to the invention. The reaction is in general carried out at temperatures between $-20°$ C. and $+120°$ C., preferably at temperatures between 0° C. and $+50°$ C.

For carrying out process (b) according to the invention, in general 1.0 to 2.0 mols, preferably equimolar amounts, of phosphines or phosphites of the formula (VI) are employed per mol of 5-azido-1-aryl-pyrazole of the formula (Ia). The reaction is carried out and the reaction products of the formula (I) are worked up and isolated by customary methods.

The compounds according to the invention of the formula (Ib)

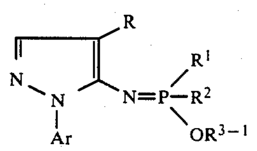

(Ib)

in which

R, $R^1$, $R^2$ and Ar have the abovementioned meaning and $R^{3-1}$ represents alkyl or cycloalkyl, or represents optionally substituted aralkyl or aryl, and which are obtainable with the aid of process (b) according to the invention are furthermore suitable as intermediate products for the preparation of other herbicides which are the subject of German patent application No. De-P 3,539,844 of Nov. 9, 1985.

Thus, compounds of the formula (XVI)

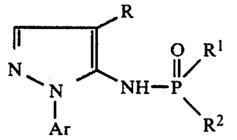

(XVI)

in which

R, $R^1$, $R^2$ and Ar have the abovementioned meaning, are obtained by a process in which compounds of the formula (Ib)

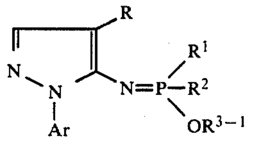

(Ib)

in which

R, $R^1$, $R^2$, $R^{3-1}$ and Ar have the abovementioned meaning, are reacted with water, if appropriate in the presence of a diluent, such as, for exampale, xylene, and if appropriate in the presence of a catalyst, such as, for example, benzoic acid, at temperatures between 50° C. and 180° C. (compare the preparation examples).

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocolyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can thereby be used with particularly good success for selectively combating monocotyledon and dicotyledon weeds in monocotyledon and dicotyledon crops, such as, for example, wheat, barley, rice or cotton.

The active compounds according to the invention moreover engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viniculture. Defoliation of the plants can also be carried out to lower the transpiration of plants before they are transplanted.

The active compounds can be converted to the customary formulations, such as solutions, emulsions, wettable powders, suspensions, powders, dusting agents, pastes, soluble powders, granules, aerosols, suspension-emulsion concentrates, natural and synthetic materials impregnated with active compound, very fine capsules in polymeric substances and in coating compositions for seed, as well as ULV formulations.

These formulations are produced in known manner, for example by mixing the active compounds with extenders, that is liquid solvents, liquefied gases under pressure and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

By liquefied gaseous extenders or carriers are meant these liquids which are gaseous at normal temperature and under normal pressure, for example aerosol propellants, such as halogenated hydrocarbons as well as butane, propane, nitrogen and carbon dioxide.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4-(1H,3H)-dione or N-(2-benzthiazolyl)-N,N'-dimethyl urea, for combating weeds in cereals; 4-amino-3-methyl-6-phenyl-1,2,4- triazin-5(4H)-one, for combating weeds in sugar beet, and 4-amino-6-(1,1-dimethylethyl)-3-methylthio-1,2,4-triazin-5(4H)-one, for combating weeds in soy beans.

Mixtures with N,N-dimethyl-N'-(3-trifluoromethyl-phenyl)-urea; N,N-dimethyl-N'-(3-chloro-4-methyl-phenyl)urea; N,N-dimethyl-N'-(4-isopropylphenyl)-urea; 4-amino-6-t-butyl-3-ethylthio-1,2,4-triazin-5-(4H)-one; 2,4-dichlorophenoxy acetic acid; 2,4-dichlorophenoxy-propionic acid; (2-methyl-4-chloro-phenoxy)-acetic acid; (4-chloro-2-methylphenoxy)-propionic acid; chloroacetic acid N-(methoxymethyl)-2,6-diethylanilide; 2-ethyl-6-methyl-N-(1-methyl-2-methoxyethyl)-chloroacetanilide; 2,6-dinitro-4-trifluoromethyl-N,N-dipropylaniline; 2-benzyloxyethyl, trimethylsilylmethyl or 2,2-diethoxyethyl 2-[4-(3,5-dichloropyrid-2-yloxy)-phenoxy]-propionate; methyl 5-(2,4-dichlorophenoxy)-2-nitrobenzoate; 3,5-diiod-4-hydroxybenzo nitrile; 3-isopropyl-2,1,3-benzothiadiazin-4-one 2,2-dioxide; 2-chloro-N-{[(4-methoxy-6-methyl-1,3,5-triazin-2-yl)-amino]carbonyl}-benzenesulfonamide; 4-ethylamino-2-t-butylamino-6-methylthio-s-triazine; 2-{4-[<3-chloro-5-(trifluoromethyl)-2-pyridyl>-oxy]-phenoxy}-propanoic acid and propanoic acid ethyl ester; 3,5-dibromo-4-hydroxy-benzonitrile; methyl 2-[4-(2,4-dichlorophenoxy)-phenoxy]-propionate; N-( 1-ethylpropyl)-3,4-dimethyl-2,6-dinitroaniline; N-methyl-2-(1,3-benzothiazol-2-yloxy)-acetanilide; S-(2,3,3-trichloro-allyl) N,N-diisopropyl-thiolcarbamate and 1-methyl-3-phenyl-5-(3-trifluoromethyl-phenyl)-4-pyridone, where appropriate, are also of advantage. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

When used as growth regulators, the active compounds according to the invention can likewise be present in the formulations as a mixture with other known active compounds, such as fungicides, insecticides, acaricides and herbicides, and in mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, coating and the like. It is furthermore possible to apply the active compounds in accordance with the ultra-low volume process or to inject the active compound preparation or the active compound itself into the soil. It is also possible to treat the seeds of plants.

When used as growth regulators, the amounts applied can likewise be varied within a substantial range. In general, 0.01 to 50 kg, preferably 0.05 to 10 kg, of active compound are used per hectare of soil surface.

As regards the time of application, the rule is that the growth regulators are used within preferred period of time, the exact definition of which depends on the climatic and vegetative circumstances.

When applied in corresponding amounts, the active compounds according to the invention moreover also show an activity as leaf insecticides.

The preparation and use of the active compounds according to the invention can be seen from the following examples:

PREPARATION EXAMPLES

Example 1

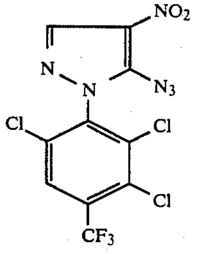

(process a−α)

1.0 g (0.015 mol) of sodium azide is added to 3.0 g (0.007 mol) of 5-bromo-4-nitro-1-(2,3,6-trichloro-4-trifluoromethyl-phenyl)-pyrazole in 50 ml of dimethylsulphoxide, the mixture is stirred at room temperature for 15 hours, poured into 150 ml of water and extracted several times with chloroform and ethyl acetate, the combined organic phases are dried over magnesium sulphate and concentrated in vacuo and the oily crude produc is purified by chromatography (silica gel; mobile phase: chloroform/acetone 9:1). 0.68 g (24% of theory) of 5-azido-4-nitro-1-(2,3,6-trichloro-4-trifluoromethyl-phenyl)-pyrazole of melting point 84° C.–88° C. is obtained.

PREPARATION OF THE STARTING COMPOUNDS

Example II-1

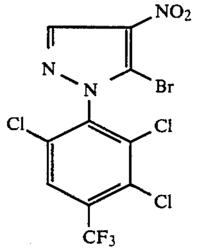

4.8 ml (0.04 mol) of t-butyl nitrite are added dropwise to 5.2 g (0.014 mol) of 5-amino-4-nitro-1-(2,3,6-trichloro-4-trifluoromethyl-phenyl)-pyrazole in 16 ml (0.18 mol) of bromoform in the course of 10 minutes, while stirring, the temperature of the reaction mixture rising to 50° C. When the addition has ended, the mixture is stirred at the reflux temperature for a further hour and concentrated in vacuo and the oil which remains is purified by column chromatography (silica gel/mobile phase: chloroform/acetone 9:1).

5.0 g (82% of theory) of 5-bromo-4-nitro-1-(2,3,6-trichloro-4-trifluoromethyl-phenyl)-pyrazole of melting point 97° C.–99° C. are obtained.

EXAMPLE VII-1

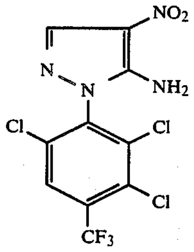

7.5 g (0.0227 mol) of 5-amino-1-(2,3,6-trichloro-4-trifluoro-methyl-phenyl)-pyrazole and 2.2 ml (2.3 g=0.023 mol) of acetic anhydride in 20 ml of glacial acetic acid are stirred at room temperature for about 4 hours, until the starting substance is no longer detectable in the thin layer chromatogram. A further 2.7 ml (2.9 g=0.0288 mol) of acetic anhydride and, at 5° C. to 10° C., 1.2 ml (1.8 g=0.028 mol) of a 98% strength nitric acid are then added, the mixture is stirred at room temperature for 8 hours, the solvent is removed in vacuo and the residue is taken up in 30 ml of ethanol and 20 ml of concentrated hydrochloric acid. The mixture is heated at the reflux temperature for 12 hours and concentrated in vacuo, the residue is taken up in 100 ml of methylene chloride, the mixture is washed carefully (evolution of $CO_2$) with 100 ml of saturated sodium bicarbonate solution and dried over magnesium sulphate and the solvent is removed in vacuo.

7.5 g (98% of theory) of 5-amino-4-nitro-1-(2,3,6-trichloro-4-trifluoromethyl-phenyl)-pyrazole of melting point 78° C. to 85° C. are obtained.

EXAMPLE XIII-1

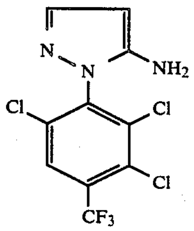

57 ml (62.7 g=0.71 mol) of 2-chloroacrylonitrile are added to 45 g (0.17 mol) of 2,3,6-trichloro-4-trifluoromethyl-phenyl-hydrazine and 35 mg (0.1 mmol) of disodium-ethylenediaminetetraacetate (Tritriplex III) in 260 ml of methanol at the reflux temperature in the course of 30 minutes, and the mixture is stirred at the reflux temperature (about 65° C.) for a further 5 hours. The reaction mixture is concentrated in vacuo, the residue is taken up in 260 ml of methanol and 15.4 ml (0.541 mol) of concentrated sulphuric acid are added dropwise at room temperature in the course of 15 minutes, while stirring. The temperature of the reaction mixture thereby rises to 32° C. When the addition has ended, the mixture is stirred at 55° C. for 30 hours and cooled to room temperature, 56 g (0.534 mol) of sodium carbonate are added, the mixture is stirred again at room temperature for 4 hours and concentrated in vacuo, the residue is taken up in 550 ml of methylene chloride, 55 ml of water are added, the mixture is stirred at room temperature for 8 hours, the organic phase is separated off, washed with 250 ml of concentrated aqueous sodium chloride solution and dried over magnesium sulphate and the solvent is removed in vacuo.

52.6 g (94% of theory) of 5-amino-1-(2,3,6-trichloro-4-trifluoromethyl-phenyl)-pyrazole of melting point 109°–114° C. are obtained.

Example IX-1

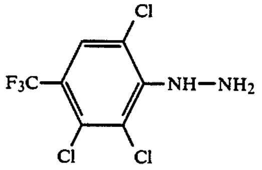

200 g (0.704 mol) of 1,2,3,4-tetrachloro-5-trifluoromethylbenzene and 240 ml (247.2 g/4.94 mol) of hydrazinehydrate in 500 ml of dioxane are heated under reflux for 14 hours. The heavier (aqueous) phase is separated off from the cooled two-phase reaction mixture and the organic phase is concentrated to dryness in vacuo. The residue is suspended in 600 ml of water and 100 ml of methylene chloride, brought to pH 10 with 10% strength aqueous sodium hydroxide solution and warmed slowly to 30° C. to 35° C., whereupon two clear phases form from the cloudy suspension. The mixture is allowed to cool to room temperature, the organic phase is separated off, washed with 200 ml of concentrated aqueous sodium chloride solution and dried over magnesium sulphate and the solvent is removed in vacuo. The crude product is stirred in boiling hexane for 3 to 4 hours, the mixture is then cooled at 0° C. to 5° C. for 15 hours and filtered cold with suction and the product is dried in vacuo at 50° C. for 2 to 3 hours.

146 g (71.2% of theory) of 2,3,6-trichloro-4-trifluoromethyl-phenylhydrazine of melting point 67° C.–70° C. and with a content, determined by gas chromatography, of 96% are obtained.

EXAMPLE 2

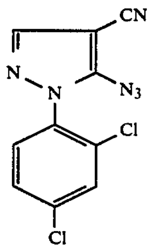

(process a-β)

10 ml of ether and then 0.85 g (0.012 mol) of sodium nitrite in 10 ml of water are added to 2.7 g (0.01 mol) of 5-hydrazino-4-cyano-1-(2,4-dichlorophenyl)-pyrazole in a solution of 1.9 ml of concentrated hydrochloric acid in 10 ml of water at 0° C. When the addition has ended, a further 20 ml of water and 30 ml of ether are added, the mixture is filtered, the ether phase is separated off, dried over calcium chloride and concentrated in vacuo and the oil thus obtainable is purified by chromatography (silica gel; mobile phase: methylene chloride/acetone 9:1). 1.2 g (43% of theory) of 5-azido-4-cyano-1-(2,4-dichlorophenyl)-pyrazole are obtained as an oil.

IR: $\nu=2260$ ($N_3$); 2190 (CN) $cm^{-1}$.

PREPARATION OF THE STARTING COMPOUNDS

Example IV-1

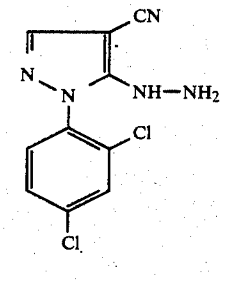

6.4 g (0.02 mol) of 5-bromo-4-cyano-1-(2,4-dichlorophenyl)-pyrazole and 15 g (0.2 mol) of hydrazine hydrate in 80 ml of dioxane are stirred at the reflux temperature for 20 hours, the mixture is then concentrated under reduced pressure and the residue is stirred with water, filtered off with suction and recrystallized twice from ethanol. 2.1 g (40% of theory) of 4-cyano-5-hydrazino-1-(2,4-dichlorophenyl)-pyrazole of melting point 199° C.-204° C. are obtained.

Example II-2

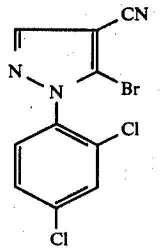

6 g (0.09 mol) of sodium nitrite in 15 ml of water are added to a suspension of 12.7 g (0.05 mol) of 5-amino-4-cyano-1-(2,4-dichlorophenyl)-pyrazole in 100 ml of hydrobromic acid at −5° C. to 0° C. and the mixture is stirred until the evolution of gas has ended, the temperature rising to 30° C. The solid residue is filtered off with suction and suspended in water and the suspension is neutralized with sodium bicarbonate and filtered off with suction again and the product is dried.

14.5 g (91.5% of theory) of 5-bromo-4-cyano-1-(2,4-dichlorophenyl)-pyrazole of melting point 84° C. (decomposition) are obtained.

Example 3

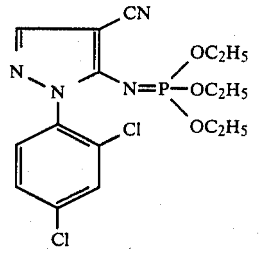

(process b)

A solution of 3.7 g (0.013 mole) of 5-azido-4-cyano-1-(2,4-dichlorophenyl)-pyrazole in 20 ml of ether is added dropwise to a solution of 2.2 g (0.013 mol) of triethylphosphite in 20 ml of ether, while stirring. For working up, the mixture is washed with water and dried over sodium sulphate and the solvent is removed in vacuo. 2.7 g (50% of theory) of 4-cyano-5-[N-(triethoxyphosphoroimido)]-1-(2,4-dichloro-phenyl)-pyrazole of melting point 50° C. are obtained.

Example 4

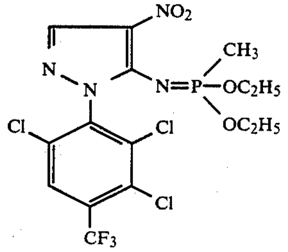

(process b)

A solution of 4.5 g (0.011 mol) of 5-azido-4-nitro-1-(2,3,6-trichloro-4-trifluoromethyl-phenyl)-pyrazole in 20 ml of ether is added dropwise to 1.7 g (0.012 mol) of diethyl methylphosphonite in 20 ml of ether. For working up, the solvent is removed in vacuo and the oil which remains is purified by chromatography (silica gel; mobile phase: methylene chloride). 2.8 g (50% of theory) of 4-nitro-5-[N-(diethoxymethyl-phosphoroimido)-1-(2,3,6-trichloro-4-trifluoromethyl-phenyl)-pyrazole of melting point 79° C.-83° C. are obtained.

The following 1-aryl-pyrazoles of the general formula (I) are obtained in a corresponding manner and in accordance with the general statements on the preparation:

TABLE 2
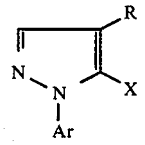
(I)
| Example No. | R | X | Ar | Melting point °C. |
|---|---|---|---|---|
| 5 | $NO_2$ | $N_3$ | 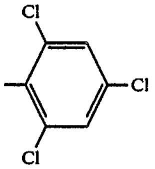 | 130 (decomposition) |
| 6 | CN | $N_3$ | 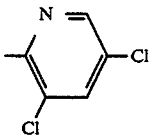 | 120 |
| 7 | $NO_2$ | $N_3$ | 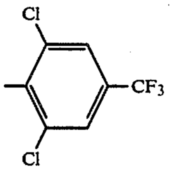 | 89 |
| 8 | CN | $N_3$ | 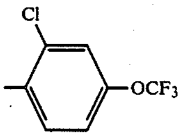 | $^1H$—NMR* 8.5 |
| 9 | $NO_2$ | $N_3$ | 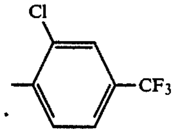 | 66 |
| 10 | $NO_2$ | $N_3$ | 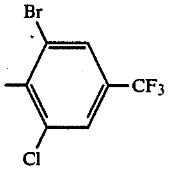 | 84–86 |
| 11 | $NO_2$ | $-N{=}P(OC_2H_5)_3$ | 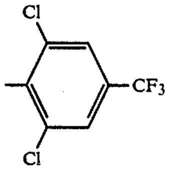 | 73 |
| 12 | CN | 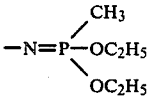 | 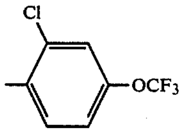 | $^1H$—NMR*: 1.7 |
*The $^1H$—NMR spectra were recorded in $CDCl_3$ with tetramethylsilane (TMS) as the internal standard. The chemical compound is quoted as the δ-value in ppm.

PREPARATION OF A SECONDARY PRODUCT

Example XVI-1

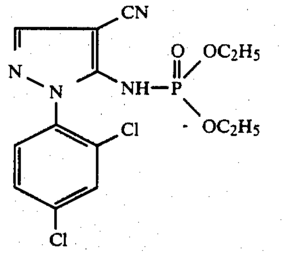

1.3 g (0.003 mol) of 4-cyano-5-[N-(triethoxyphosphoroimido)]-1-(2,4-dichlorophenyl)-pyrazole and 0.5 g (0.004 mol) of benzoic acid are heated at 150° C. in 20 ml of xylene with a little water for 3 days. For working up, the solvent is removed in vacuo, the residue is taken up in methylene chloride, the mixture is washed in each case twice with aqueous sodium bicarbonate solution and water, dried over sodium sulphate and concentrated in vacuo and the residue is purified by chromatography (silica gel; mobile phase: methylene chloride-/acetone 9:1). 0.4 g (35% of theory) of 4-cyano-5-[N-(O,O-diethylphosphoryl)amino]-1-(2,4-dichlorophenyl)-pyrazole of melting point 70° C. is obtained.

USE EXAMPLES

The compound shown below was employed as a comparison substance in the use examples which follow:

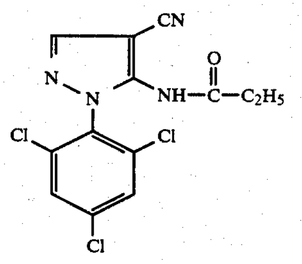

(A)

4-cyano-5-propionamido-1-(2,4,6-trichloro-phenyl)-pyrazole (known from DE-OS (German Published Specification) No. 3,226,513).

EXAMPLE A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)

100% = total destruction

In this test, a clearly superior activity and crop plant selectivity compared with comparison substance (A) is shown, for example, by the compound according to preparation Examples (1), (4), (7) and (10).

EXAMPLE B

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied to 2,000 l of water/ha. After three weeks, the degree of damage to the plants is rated in % damage in comparison to the development of the untreated control. The figures denote:

0% = no action (like untreated control)

100% = total destruction

In this test, a clearly superior activity and crop plant selectivity compared with comparison substance (A) is shown, for example, by the compound according to preparation Examples 1, 4 and 7.

EXAMPLE C

Defoliation and desiccation of the leaves of cotton

Solvent: 30 parts by weight of dimethylformamide

Emulsifier: 1 part by weight of polyoxyethylene sorbitan monolaurate

To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. In this stage, the plants are sprayed with the preparations of active compound until dripping wet. After 1 week, the shedding of leaves and the desiccation of the leaves are rated, in comparison with the control plants.

In this test, a clear effectiveness as defoliant and desiccant is shown, for example, by the compound according to preparation Example 7.

It is understood that the specification and examples are illustrative but not limitative of the present invention and that other embodiments within the spirit and scope of the invention will suggest themselves to those skilled in the art.

We claim:

1. A 1-aryl-pyrazole of the formula

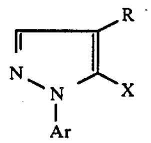

in which

R represents cyano or nitro,

Ar represents phenyl, 2-pyridyl, 3-pyridyl or 4-pyridyl, in each case optionally monosubstituted or polysubstituted by identical or different substituents selected from the group consisting of cyano, nitro, halogen, in each case straight-chain or branched alkyl, alkoxy or alkoxycarbonyl with in each case up to 4 carbon atoms, in each case straight-chain or branched halogenoalkyl or halogenoalkoxy with in each case 1 to 4 carbon atoms and 1 to 9 identical or different halogen atoms and the radical $-S(O)_n-R^4$, X represents an azido group, or represents the radical

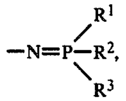

$R^1$, $R^2$ and $R^3$ independently of one another represent in each case straight-chain or branched alkyl, alkenyl, or alkinyl with in each case up to 8 carbon atoms, or represent straight-chain or branched halogenoalkyl with 1 to 6 carbon atoms and 1 to 13 identical or different halogen atoms, or represent straight-chain or branched alkoxyalkyl with in each case 1 to 4 carbon atoms in the individual alkyl parts, or represent straight-chain or branched alkoxy with 1 to 6 carbon atoms, or represent cycloalkyl or cycloalkoxy with in each case 3 to 7 carbon atoms, or represent aralkyl, aralkoxy, aryl or aryloxy with in each case 6 to 10 carbon atoms in the individual aryl parts and, where appropriate, 1 to 3 carbon atoms in the straight-chain or branched alkyl parts and in each case optionally monosubstituted or polysubstituted by identical or different substituents in the aryl parts, substituents on the aryl in each case being halogen, cyano, nitro and in each case straight-chain or branched alkyl, alkoxy, alkylthio or halogenoalkyl with in each case 1 to 4 carbon atoms and, in case of the halogenoalkyl, with 1 to 9 identical or different halogen atoms, $R^4$ represents amino, or represents in each case straight-chain or branched alkyl, alkylamino dialkylamino or halogenoalkyl with in each case up to 4 carbon atoms in the individual alkyl parts and, in case of the halogenoalkyl, with up to 9 identical or different halogen atoms, and n represents the number 0, 1 or 2, but wherein, in the case where R represents cyano and X simulaneously represents an azido group, Ar does not represent unsubstituted phenyl and does not represent 5-nitro-2-pyridyl.

2. A 1-aryl-pyrazole according to claim 1, in which

Ar represents phenyl which is optionally mono-, di-, tri-, tetra- or pentasubstituted by identical or different substituents, or represents 2-pyridyl which is optionally mono-, di-, tri- or tetrasubstituted by identical or different substituents in each case selected from the group consisting of cyano, nitro, fluoro, chloro, bromo, iodo, methyl, ethyl, n- and i-propyl, n-, i-, s- and t-butyl, or represents methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy trifluorodichloroethoxy, pentachloroethoxy and the radical $-S(O)_n-R^4$, $R^1$, $R^2$ and $R^3$ independently of one another each represent methyl, ethyl, n- or i-propyl, n-, i-, s- or t-butyl, allyl, propargyl, chloromethyl, dichloromethyl, trichloromethyl, fluoromethyl, dichlorofluoromethyl, trifluoromethyl, dichlorofluoromethyl, difluorochloromethyl, chloroethyl, trichloroethyl, pentachloroethyl, trifluoroethyl, pentafluoroethyl, bromoethyl, methoxymethyl, methoxyethyl, ethoxymethyl, ethoxyethyl, n-propoxymethyl, i-propoxymethyl, n-propoxyethyl, i-propoxyethyl, methoxy, ethoxy, n- or i-propoxy, n-, i-, s- or t-butoxy, chlcopropyl, cyclopentyl, cyclohexyl or cyclohexyloxy, or represents benzyl, benzyloxy, phenyl or phenoxy, in each case optionally mono-, di-, tri-, tetra- or pentasubstituted by identical or different substituents, substituents on the aryl in each case being fluorine, chlorine, bromine, cyano, nitro, methyl, ethyl, methoxy, methylthio and trifluoromethyl, $R^4$ represents amino, methylamino, ethylamino, dimethylamino, diethylamino, fluorodichloromethyl, difluoromethyl, tetrafluoroethyl, trichloroethyl, trifluoromethyl, methyl or ethyl, and n represents the number 0, 1 or 2.

3. A compound according to claim 2, wherein such compound is 4-nitro-5-[N-(diethoxymethyl-phosphoroimido)]-1-(2,3,6-trichloro-4-trifluoromethyl-phenyl)-pyrazole of the formula

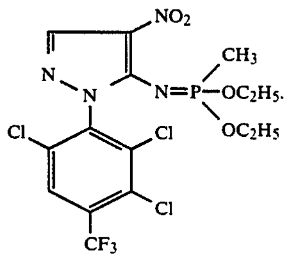

4. A compound according to claim 1, wherein such compound is 5-azido-4-nitro-1-(2-chloro-4-trifluoromethylphenyl)-pyrazole of the formula

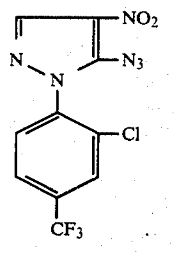

5. A compound according to claim 1, wherein such compound is 5-azido-4-nitro-1-(2-bromo-6-chloro-4-trifluoromethyl-phenyl)-pyrazole of the formula

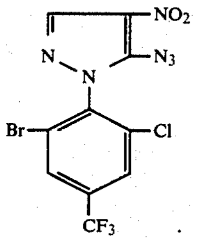

6. A herbicidal or plant growth-regulating composition comprising a herbicidally or plant growth-regulating effective amount of a compound according to claim 1 and a diluent.

7. A method of combating unwanted vegetation which comprises applying to such vegetation or to a locus from which it is desired to exclude such vegetation a herbicidally effective amount of a compound according to claim 1.

8. The method according to claim 7, wherein such compound 4-nitro-5-[N-(diethoxymethyl-phosphoroimido)]-1-(2,3,6-trichloro-4-trifluoromethyl-phenyl)-pyrazole, 5-azido-4-nitro-1-(2-chloro-4-trifluoromethyl-phenyl)-pyrazole or 5-azido-4-nitro-1-(2-bromo-6-chloro-4-trifluoromethyl-phenyl)-pyrazole.

9. A method of regulating the growth of plants which comprises applying to such plants or to a locus in which such plants are growing or are to be grown a plant growth-regulating effective amount of a compound according to claim 1.

10. A method according to claim 9, wherein such compound is 4-nitro-5-[N-(diethoxymethyl-phosphoroimido)]-1-(2,3,6-trichloro-4-trifluoromethyl-phenyl)pyrazole, 5-azido-4-nitro-1-(2-chloro-5-trifluoromethyl-phenyl)-pyrazole or 5-azido-4-nitro-1-(2-bromo-6-chloro-4-trifluoromethyl-phenyl)-pyrazole.

* * * * *

UNITED STATES PATENT AND TRADEMARK OFFICE

CERTIFICATE OF CORRECTION

PATENT NO. : 4,770,688

DATED : September 13, 1988

INVENTOR(S) : Reinhold Gehring, et al

It is certified that error appears in the above-identified patent and that said Letters Patent is hereby corrected as shown below:

| | |
|---|---|
| Col. 1, line 11 | Correct --propionamido-- |
| Col. 9, line 35 | Delete "application" and substitute --applications-- |
| Col. 10, line 33 | After "amino," insert --or-- |
| Col. 11, line 36 | After "Chemistry" delete ")" |
| Col. 11, line 64 | Correct spelling of --halogeno-aromatics-- |
| Col. 12, line 17 | Insert --They are obtained by a process in which 5-halogeno-1-aryl-pyrazoles of the formula (II)-- |
| Col. 14, line 23 | Delete "De-P" and substitute --DE-P-- |
| Col. 16, line 20 | Delete "these" and substitute --those-- |
| Col. 18, line 40 | Delete "produc" and substitute --product-- |
| Col. 19, line 37 | Delete "98%" and substitute --84%-- |
| Col. 19, line 56 | Correct spelling of --Titriplex-- |
| Col. 22, line 60 | After "phoroimido)" insert --]-- |
| Col. 28, line 49 | Delete "claim 2" and substitute --claim 1-- |

UNITED STATES PATENT AND TRADEMARK OFFICE

CERTIFICATE OF CORRECTION

PATENT NO. : 4,770,688

DATED : September 13, 1988

INVENTOR(S) : Reinhold Gehring, et al

It is certified that error appears in the above-identified patent and that said Letters Patent is hereby corrected as shown below:

Col. 30, line 9 After "compound" insert --is--

Signed and Sealed this

Twenty-third Day of May, 1989

Attest:

DONALD J. QUIGG

*Attesting Officer*

*Commissioner of Patents and Trademarks*